(12) United States Patent
Barradine et al.

(10) Patent No.: US 7,211,403 B2
(45) Date of Patent: May 1, 2007

(54) ASSAY USING POROSITY-REDUCTION TO INHIBIT MIGRATION

(75) Inventors: Martin Barradine, Kingston-Upon-Thames (GB); Tracey Gurmin, Kingston-Upon-Thames (GB)

(73) Assignee: Genosis Limited, Kingston-Upon-thames (GB)

( * ) Notice: Subject to any disclaimer, the term of this patent is extended or adjusted under 35 U.S.C. 154(b) by 666 days.

(21) Appl. No.: 10/145,170

(22) Filed: May 13, 2002

(65) Prior Publication Data

US 2002/0127614 A1   Sep. 12, 2002

Related U.S. Application Data

(63) Continuation of application No. 09/658,148, filed on Sep. 8, 2000, now Pat. No. 6,472,226, which is a continuation of application No. PCT/GB99/03249, filed on Oct. 1, 1999.

(30) Foreign Application Priority Data

Oct. 2, 1998 (GB) ................................. 9821526.2

(51) Int. Cl.
*G01N 33/53* (2006.01)
(52) U.S. Cl. ................. 435/7.21; 435/7.1; 435/805; 435/7.94
(58) Field of Classification Search ................. 435/7.1, 435/7.2, 2, 7.3, 7.94, 325, 331, 287.2, 806, 435/970
See application file for complete search history.

(56) References Cited

U.S. PATENT DOCUMENTS

| | | | |
|---|---|---|---|
| 4,857,453 A | 8/1989 | Ullman et al. ................. 435/7 |
| 5,087,556 A * | 2/1992 | Ertinghausen ............... 435/7.9 |
| 5,244,630 A | 9/1993 | Khalil et al. ................... 422/52 |
| 5,310,650 A | 5/1994 | McMahon et al. ............. 435/6 |
| 5,741,662 A | 4/1998 | Madsen et al. ................ 435/34 |
| 5,763,262 A | 6/1998 | Wong et al. ............. 435/287.2 |
| 5,824,268 A * | 10/1998 | Bernstein et al. ............. 422/56 |
| 6,036,919 A | 3/2000 | Thym et al. ................... 422/58 |
| 6,197,598 B1 | 3/2001 | Schrier et al. ............. 436/518 |
| 6,632,603 B1 * | 10/2003 | Hubscher et al. ............... 435/6 |
| 6,753,189 B1 * | 6/2004 | Narahara et al. ........... 436/514 |

FOREIGN PATENT DOCUMENTS

EP    0293779 A1   12/1988

(Continued)

*Primary Examiner*—Bao-Thuy L. Nguyen
(74) *Attorney, Agent, or Firm*—Jenkens & Gilchrist, PC

(57) ABSTRACT

Device for assaying an analyte, comprising a labelling zone, where a label can bind to the analyte, in communication with a capture zone, wherein the pore size of the capture zone is such that label which is not bound to the analyte can migrate therethrough, whereas label which is bound to the analyte cannot. During migration from the labelling zone (large pore size) to the capture zone (small pore size), unbound label can pass into and through the capture zone, whereas bound label will be captured at the junction of the labelling zone and the capture zone. The device relies upon the label being smaller than the analyte, such that free label is not retarded by the capture zone. It is particularly suitable for assaying analytes such as spermatozoa, which are large in comparison with a label such as a labelled antibody.

16 Claims, 2 Drawing Sheets

FOREIGN PATENT DOCUMENTS

| | | | |
|---|---|---|---|
| EP | 0 387 873 | * | 3/1990 |
| EP | 0387696 A2 | | 9/1990 |
| EP | 0613005 A2 | | 8/1994 |
| WO | WO 88/08534 | * | 11/1988 |
| WO | WO 94/16329 | | 7/1994 |
| WO | WO 97/06439 | | 2/1997 |

* cited by examiner

ASSAY USING POROSITY-REDUCTION TO INHIBIT MIGRATION

This application is a continuation of U.S. application Ser. No. 09/658,148, filed Sep. 8, 2000 now U.S. Pat. No. 6,472,226, which is a continuation of International Application No. PCT/GB99/03249 filed on Oct. 1, 1999, which claims the benefit of British Patent Application No. 9821526 filed on Oct. 2, 1998.

TECHNICAL FIELD

This invention relates to assay devices for measuring analytes. In particular, it relates to devices which capture analytes mechanically within a porous material, rather than using conventional immuno-capture techniques.

BACKGROUND ART

The format of the standard rapid test lateral flow device has remained unchanged for around ten years. Typically, the device will comprise a nitrocellulose strip. Sample is applied to an application zone, from which it flows by capillary action through a zone containing a visibly-labelled antibody specific for the analyte in question. Free and bound label continue to migrate to a capture zone, where immobilised antibody specific for the analyte binds the analyte-label complex. Free label (unbound antibody) continues to migrate, leaving an analyte-specific signal in the capture zone. These types of lateral flow device are disclosed in, for example, EP-A-0284232. Numerous variations to the basic assay have been described, including those in WO92/12428, EP-A-0613005, WO97/06439, and U.S. Pat. No. 5,741,662.

In all cases, however, capture of the analyte-label complex is mediated by an immobilised reagent, which is typically an antibody that is specific for the analyte. This is unsatisfactory in many respects.

Firstly, manufacturing quality control is difficult. The solid phase capture membrane is typically made from nitrocellulose, and antibodies are applied to the membrane directly. Nitrocellulose manufacture is not, however, homogeneous. Quality control of the solid phase antibody is therefore limited to testing a statistical sample of devices from the same, but heterogeneous, batch, and assuming that the whole batch will perform within specific tolerances. It is well known, however, that membranes vary considerably, even within a single batch or lot number.

Secondly, they are relatively cumbersome to manufacture. The application of immobilised antibody to the strip requires a separate step from the application of the mobile labelled antibody. The capture antibody can be sprayed directly onto the nitrocellulose strip, but the label antibody has to be soaked into material which is subsequently attached to the nitrocellulose strip, with an overlap to ensure capillary flow.

Thirdly, antibody is immobilised by spraying a solution onto a membrane. Some of the antibody does not bind to the membrane strongly, however, and some remains loosely associated with immobilised antibody. This semi-bound or unbound antibody can become mobile when the solvent front passes over it, resulting in lower binding of label at the detection zone. If the device includes a control line, this will capture the additional label which should have been captured at the detection zone. Tests that rely on a comparison of colour intensity between control and detection lines, such as ovulation prediction kits, may therefore give false results. Furthermore, application by spraying inevitably leads to diffusion into the membrane, leading to a more diffuse and less focused detection signal.

Fourthly, the sensitivity of the devices is limited by their format. Analyte and labelled-antibody react as they migrate through the membrane, and flow rates are therefore adjusted to enable the labelled-antibody to flow at the solvent front in order to maximise the amount of time in which the analyte-label complex can form. The complex passes over the capture antibody for a short time, however, thus imposing constraints on the design of the test and its performance characteristics. The short reaction time decreases sensitivity, and also means that high affinity capture antibodies are required.

Finally, the shelf-life of these test devices is often limited by the collapse of the immobilised capture antibody onto the membrane over time.

These shortcomings in the prior art devices are addressed by the present invention, which does not use immobilised antibody to capture an analyte-label complex.

DISCLOSURE OF THE INVENTION

The invention provides a device for assaying an analyte, comprising a labelling zone, where a label can bind to the analyte, in communication with a capture zone, wherein the pore size of the capture zone is such that label which is not bound to the analyte can migrate therethrough, whereas label which is bound to the analyte cannot.

During migration from the labelling zone to the capture zone, unbound label can pass into and through the capture zone, whereas bound label will be captured at the junction of the labelling zone and the capture zone. A comparison of the amount of label captured at the entrance to the capture zone with the amount migrating through the capture zone allows the level of analyte to be assessed—as analyte concentration increases, the amount of label retained at the junction of the labelling zone and the capture zone also increases.

It will be apparent that the invention relies upon the label being smaller than the analyte, such that free label is not retarded by the capture zone.

The device is particularly suitable for assaying analytes such as biological cells, which are large in comparison with a label such as a labelled antibody. Preferred cells for assay are spermatozoa and micro-organisms, such as bacteria.

The labelling zone is where label comes into contact with the analyte. It is preferably formed from fibrous material, such as a pad of HDPE material, bonded polyester fibre, glass fibre, or the like. The pore size should be large enough to allow the analyte to move relatively freely, in contrast to the pore size of the capture zone.

The label is typically an antibody which can bind to the analyte of interest, and which has been suitably labelled. The label is preferably visible to the naked eye eg. a fluorescent label, or a particulate label such as colloidal gold (which is visible as a pink colour), or a stain such as eosin. It will be appreciated that the term 'antibody' may include polyclonal and monoclonal antibodies, as well as antibody fragments (eg. F(ab)$_2$, Fc etc.), provided that the necessary biological specificity is retained.

The capture zone can be made from any suitable porous material through which unbound label can migrate, whilst analyte-bound label cannot. This requirement is reflected in the pore size of the capture zone. In one embodiment, the capture zone will be made from HDPR with a nominal pore size of around 1–75 µm, preferably 10–50 µm, and more preferably 20–35 µm. In second embodiment, the capture zone will be made from nitrocellulose, with a nominal pore size of around 1–15 µm, preferably 3–10 µm, and more preferably 5–8 µm.

In some embodiments, the labelling zone and capture zone may be formed from a single piece of porous material, which contains a region of reduced pore size. By crushing or compressing a region of a porous material, for instance, the pore size can be reduced such that an analyte-bound label cannot enter the compressed region ie. to form a capture zone. As an alternative, the pores of the material could be partially blocked, to achieve the same effect.

As is well known to those in the art, the nominal pore size of a porous material can be determined by hard particle challenge testing ie. by determining the maximum diameter of spherical particles which can pass through the material. Alternatively, the pore size of a material may be determined by measuring its 'bubble point'. The bubble point is the pressure required to force air through a (water) wet membrane, and correlates with the pore size as measured by particle retention (although at extremes of pressure and pore size, the correlation may be weaker). The bubble point is generally easier to measure than particle retention and is thus the preferred test when assessing pore size.

When the device of the present invention is to be used for detecting and measuring a motile analyte in particular (such as motile spermatozoa or motile bacteria), the appropriate pore size may be determined empirically by routine testing.

In preferred embodiments, the capture zone includes a region which retains label which is not bound to the analyte (a 'label control' region). This will typically comprise antibody fixed within the capture zone which can bind to the analyte-specific label. Label which passes through the capture zone, rather than being captured on entry thereto, is thus retained within the 'label control' region, where it can be measured. If the analyte-specific label is a murine monoclonal antibody, for instance, then the capture zone may include a region containing immobilised anti-mouse antibody. Unbound label is thus retained either at the junction of the labelling zone and the capture zone or at the 'label control' region. A comparison of the amount of label in these two positions allows the amount of analyte in the original sample to be assessed.

In an alternative arrangement, the device might utilise two separate labelled antibodies in the labelling zone, only one being analyte-specific. The label which does not recognise the analyte is instead specific for the antibody in the 'label control' region. This label passes through the capture zone and is retained at the 'label control' region, giving a standard for comparison with the analyte-specific signal at the entrance to the capture zone; the analyte-specific label does not bind the 'label control' antibody, and continues to migrate.

The interface between the labelling zone and the capture zone is preferably narrow compared to the length of the capture zone. Where the labelling zone and the capture zone are formed from strips of overlapping material, a narrow interface between them can be achieved by the presence of a non-porous material covering the majority of the overlap. By ensuring that the interface between the labelling zone and the capture zone is narrow, the analyte-label complex is focused at the junction of the labelling zone and the capture zone, giving a sharper signal.

The analyte is preferably spermatozoa. The label preferably recognises a surface antigen which is present on the majority of a population of spermatozoa, rather than a subset. Whilst any surface antigen may be used, therefore (eg. P34H (WO97/40836), SP-10 (WO95/29188), see also EP-A-0387873), 'universal' antigens such as CD59 are preferably used. It will be appreciated that, where the antigen is not sperm-specific (ie. it is also present on other cell types, such as CD59), the sample being analysed may require treatment to remove non-spermatozoa cells. The capture zone for retarding the migration of spermatozoa is preferably a nitrocellulose membrane with a nominal pore size in the region of 5 µm–8 µm. A sperm sample may be treated to separate motile and non-motile cells before analysis (eg. see international patent applications PCT/GB99/01929 and PCT/GB99/02685). The device of the invention can be used to determine the relative numbers of motile and non-motile cells in a given sample by comparing results after such a separation. The device of the invention may comprise means to separate motile spermatozoa from non-motile spermatozoa before entry to the capture zone such that, after operation, three signals are apparent—one where label has bound non-motile cells, one where label has bound motile cells, and one of free label. It is not always necessary to separate cells in this way, however eg. in vasectomy verification, a test can simply indicate overall levels of spermatozoa, motile or not. Typically, the sperm-containing sample to be analysed will not be 'neat' semen, but will be diluted, and possibly treated to remove non-spermatozoa cells. If 'neat' semen is analysed, it will generally be necessary to use a sperm-specific label, so that non-spermatozoa cells are not labelled.

As an alternative, the analyte may be a micro-organism. The micro-organism might be a bacterium, such as enterotoxigenic *E.coli* ('ETEC') [eg. see Levine (1987) *J. Infect. Dis* 155:377-289], for which any suitably-labelled ETEC-specific antibody can be used as the label eg. gold-conjugated anti-CFA/I monoclonals. The micro-organism might be a yeast, such as *Candida*.

In preferred embodiments, migration of a sample to the capture zone is assisted by a wick before the labelling zone and/or a wick after the capture zone, to aid capillary movement.

In some embodiments of the invention, a sample might be applied directly to the capture zone. In this arrangement, label will migrate from the labelling zone through the capture zone, in which the sample is encountered. Label will be retained by analyte which has been retarded in the capture zone, and unbound label will continue to migrate.

The device of the invention can be produced simply and cheaply, conveniently in the form of a test strip or dipstick. Furthermore, it can be used very easily, for instance by the home user. The invention thus provides an assay device which can be used at home as a basic screen of, for instance, male fertility.

MODES FOR CARRYING OUT THE INVENTION

EXAMPLE 1

A Basic Lateral Flow Test Device

Figure 1:
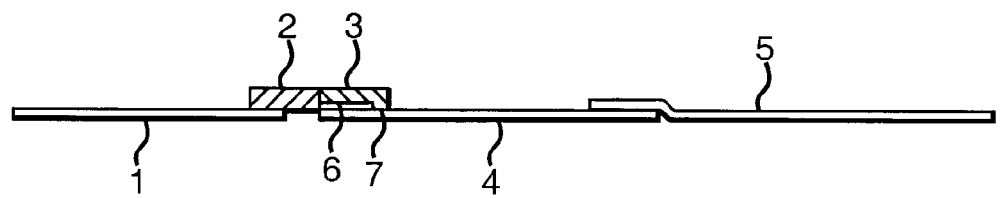
FIG. 1 shows a lateral flow device according to the invention.
Figure 1:
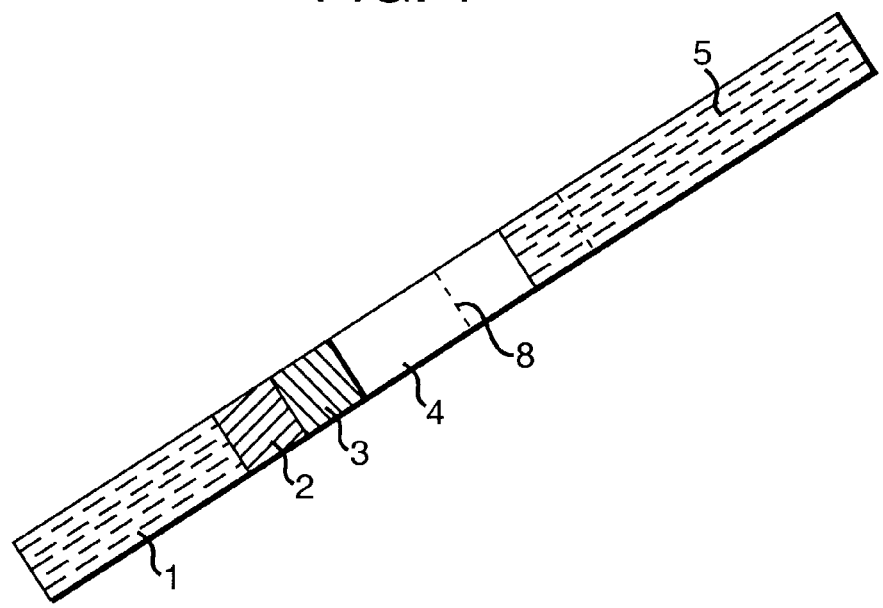

The device shown in FIG. 1 comprises a strip of filter paper (1), a first absorbent pad (2) containing gold-labelled anti-spermatozoa labelling antibody, a second absorbent pad (3) for receiving a sperm-containing sample, a nitrocellulose membrane (4), and an upper wick (5). Between the absorbent pad (3) and the nitrocellulose membrane (4) is a thin acetate strip (6) which prevents contact between the pad (3) and membrane (4) except for a narrow margin (7). Membrane (4) includes a line (8) of immobilised antibody which can react with unbound anti-sperm labelling antibody.

The nitrocellulose membrane (4) measures 5 mm×25 mm, and is mounted on a stiff plastic backing measuring 5 mm×73 mm. At one end of the membrane (4), upper wick (5), measuring 5 mm×30 mm, is attached such that they overlap by 5 mm, and at the other end a thin acetate strip (6) measuring 5 mm×4 mm is affixed. Absorbent pad (3), measuring 5 mm×5 mm is placed over acetate strip (6), such that it contacts the nitrocellulose strip (4) with a 5 mm×1 mm margin. Absorbent pad (2), measuring 5 mm×5 mm, is attached such that it abuts both pad (3) and strip (6); filter paper (1), measuring 20 mm×5 mm is attached so that it overlaps by 2 mm beneath absorbent pad (2).

Filter paper (1) is Ahlstrom blotting grade paper number 222. Absorbent pad (2) is HDPE conjugate material, thickness 0.6 mm, nominal pore size 99 μm (Sintair Ltd, England). This was saturated with a solution of monoclonal anti-CD59 antibody (Bristol University, UK) conjugated to 40 nm gold particles (diluted in purified water containing 5% trehalose, 0.1% Triton-X (Sigma) and 1% BSA) and then dried completely under vacuum. Absorbent pad (3) is made from the same HDPE material, but was saturated with 1% BSA and 0.1% Triton-X at pH 6.6, and then dried. The nitrocellulose membrane (4) is an Advanced MicroDevices 8 μm nitrocellulose membrane (CNPF-S1-L2-H50, lot number HF322228/731). Upper wick (5) is formed from Whatman chromatography paper (catalogue number 3MM CHR, lot number 3030640), left untreated as supplied.

A thin line (8) of control antibody [Jackson's AffiniPure goat anti-mouse IgG, FC and fragment specific (minimum cross-reaction with human, bovine and horse serum proteins; code 115-005-071, lot 36019), diluted to 0.02 mg/ml in 2 mM phosphate and 0.017% BSA] was immobilised on membrane (4) between the margin (7) and upper wick (5).

To use the device, a sperm-containing specimen is applied to absorbent pad (3), and filter paper (1) is placed in an appropriate buffer or the like. The buffer migrates through filter paper (1) and absorbent pad (2), bringing the gold-conjugated antibody into contact with any spermatozoa in pad (3). As the solution migrates through pad (3), towards margin (7), the antibody can bind to the sample. Labelled spermatozoa cannot pass through the nitrocellulose membrane (4), due to its small pore size, so are instead retarded around margin (7). Margin (7) thus serves as a 'choking zone' which captures material which is too large to pass through the pores of membrane (4). Unbound gold-conjugated antibody, however, will continue to migrate through the membrane until it reaches antibody line (8), which binds gold-conjugated antibody. At this stage, therefore, there may be two lines visible—one at the 'choking zone' (7), where migration of the label has been retarded by binding to spermatozoa, and one at line (8), where migration has been retarded by binding to the immobilised control antibody.

EXAMPLE 2

Qualitative Sperm Testing

In a test experiment, two samples were tested—the first was a sample of motile spermatozoa in HEPES buffer (obtained by indirect swim up from the ejaculate of a fertile man), and the second was just HEPES buffer. 75 μl of each sample was placed on the absorbent pad (3) of two separate devices, and these were placed in separate wells, each containing 75 μl HEPES.

After 15 minutes, the device used with the first sample had developed two clear red lines on membrane (4), the first about 1 mm above the absorbent pad (3), the second at line (8). The other device, however, contained a single red line at line (8). The device is thus able to capture spermatozoa mechanically around the 'choking zone'.

EXAMPLE 3

Quantitative Sperm Testing

In a further experiment, a sample of motile spermatozoa in HEPES buffer was obtained by indirect swim up from the ejaculate of a fertile man. The number of motile sperm per ml in the HEPES portion of the swim up was established using a counting chamber and found to be 3.5 million. This sample was diluted with HEPES to give four further samples with 2, 1, 0.5 and 0.25 million sperm per ml respectively. 75 μl of each of these five samples were placed on the absorbent pads (3) of five separate devices and these were placed in separate wells containing 75 μl HEPES. Buffer alone was used as a control.

Figure 2:
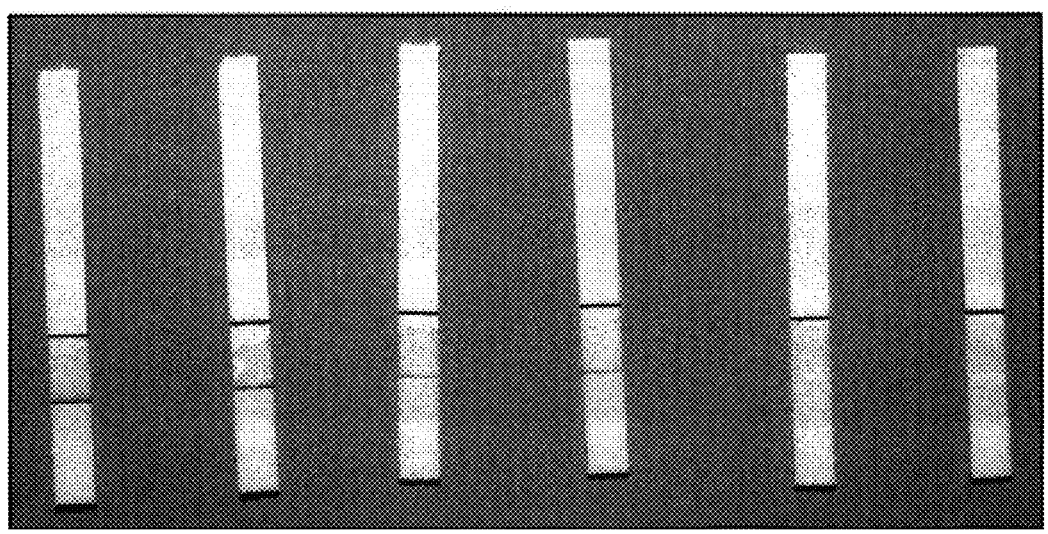
FIG. 2 shows the results of a dose-response curve experiment using this device.

After 15 minutes, each of the devices had developed two clear red lines on membrane (4), the first about 1 mm above the absorbent pad (3), the second at line (8). As clearly shown in FIG. 2, however, the intensity of the first line decreased as the number of spermatozoa in the sample decreased by dilution. No first line was visible on the control. The device is thus able to demonstrate a dose response capture around the 'choking zone'.

Further Embodiments

It will be understood that the invention is described above by way of example only and modifications may be made whilst remaining within the scope and spirit of the invention.

The invention claimed is:

1. A method for assaying biological cells, comprising the steps of:
   i) applying a sample suspected of containing said cells to a lateral flow device, the device comprising:
      (a) a labeling zone containing at least one label which binds to the cells in their presence, and through which the cells can flow; in communication with:
      (b) a porous capture zone having a pore size such that all or substantially all of the label which is not bound to the cells can flow therethrough, whereas all or substantially all cell-bound label cannot;
   ii) allowing said cells to migrate from the labeling zone to the capture zone, such that cell-bound label is captured at an interface between the labeling zone and the capture zone; and
   iii) observing the label captured at the interface.

2. The method according to claim 1, wherein the label is a labeled antibody which can bind to the cells.

3. The method according to claim 2, wherein the label is visible to the naked eye.

4. The method according to claim 3, wherein the antibody is labeled with colloidal gold.

5. The method according to claim 1, wherein the label is a dye.

6. The method according to claim 1, wherein the capture zone is nitrocellulose.

7. The method according to claim 1, wherein the labeling zone and capture zone are formed from a single piece of porous material which contains a region of reduced pore size.

8. The method according to claim 1, wherein the capture zone includes a region of immobilized antibody which binds label not bound to cells.

9. The method according to claim 1, wherein the interface between the labeling zone and the capture zone is narrow compared to the length of the capture zone.

10. The method according to claim 1, wherein the cells are spermatozoa.

11. The method according to claim 1, wherein the cells are micro-organisms.

12. The method according to claim 1, wherein flow of a sample to the capture zone is assisted by at least one of a wick before the labeling zone and a wick after the capture zone.

13. The method according to claim 1, wherein the device is in the form of a test strip or dipstick.

14. A method for assaying a biological analyte in a sample, comprising:
   i) applying a sample suspected of containing said cells to a lateral flow device, the device comprising:
      (a) a first region containing at least one label adapted to bind to the analyte;
      (b) a second region in fluid communication with the first region, the second region having a reduced pore size,
   ii) binding substantially all of the analyte in the sample to the at least one label,
   iii) allowing the sample to migrate to the second region,
   iv) sorting the sample by size such that all or substantially all of the label bound analyte are mechanically captured at an interface between the first region and the second region, and all or substantially all unbound label can flow through the second region, and
   v) observing the label at an interface between the first and second regions.

15. The method of claim 14 wherein binding substantially all of the analyte in the sample to label comprises applying the sample to the first region containing label adapted to bind to the analyte.

16. The method of claim 15 further comprising comparing the amount of label in the first region with the amount of label that has passed through the second region to determine the amount of analyte in the sample.

* * * * *